United States Patent [19]

Dickakian

[11] Patent Number: 5,332,842
[45] Date of Patent: Jul. 26, 1994

[54] PROCESS FOR INHIBITING OXIDATION AND POLYMERIZATION OF FURFURAL AND ITS DERIVATIVES

[75] Inventor: Ghazi Dickakian, Kingwood, Tex.

[73] Assignee: Exxon Chemical Patents Inc., Linden, N.J.

[21] Appl. No.: 60,871

[22] Filed: May 13, 1993

[51] Int. Cl.$^5$ .............. C07D 307/48; C10G 21/16; C10G 29/22
[52] U.S. Cl. .............. 549/490; 208/18; 208/291
[58] Field of Search .............. 549/490; 208/18, 291

[56] References Cited

U.S. PATENT DOCUMENTS

| | | | |
|---|---|---|---|
| 2,446,728 | 8/1948 | Thodos | 549/490 |
| 3,800,002 | 3/1974 | Chikatsu et al. | 203/9 |
| 4,466,905 | 8/1984 | Butler et al. | 252/403 |

Primary Examiner—Bernard Dentz
Assistant Examiner—Ba K. Trinh
Attorney, Agent, or Firm—Robert L. Graham

[57] ABSTRACT

Dialkylphenylenediamines are used to inhibit oxidation and polymerization of furfural or furfural derivatives. The preferred use of the inhibitor is in the solvent refining of lubricating oils using furfural to extract constituents from the lubricating oils.

14 Claims, 1 Drawing Sheet

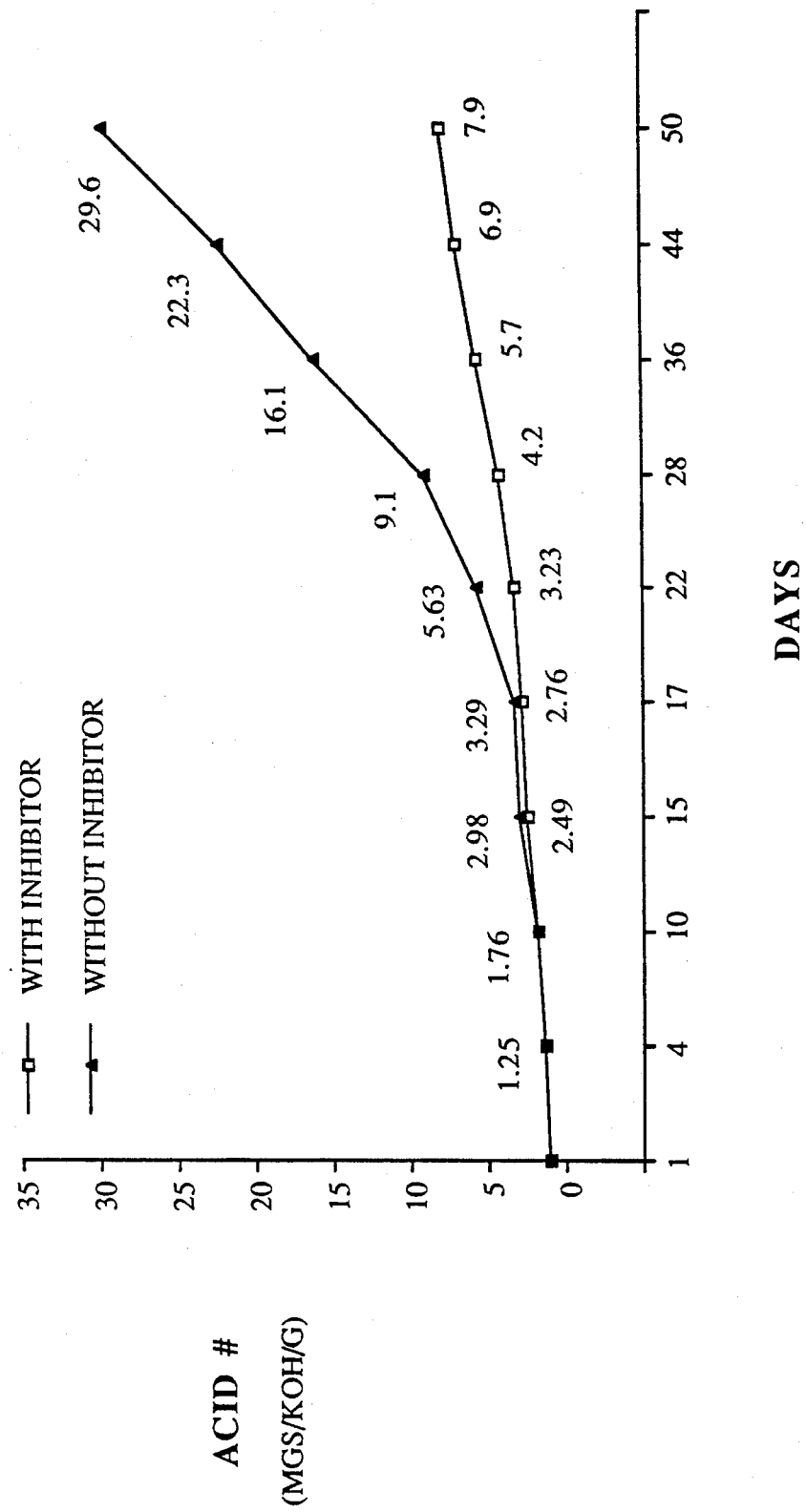

PROCESS FOR INHIBITING OXIDATION AND POLYMERIZATION OF FURFURAL AND ITS DERIVATIVES

BACKGROUND OF THE INVENTION

This invention relates generally to inhibitors for retarding oxidation and polymerization of furfural and its derivatives. In one aspect, the invention relates to a method of inhibiting furfural and its derivatives by the use of phenylenediamines and naphthalenediamines and their derivatives. In a preferred embodiment, dialkyl phenylenediamines are used.

Furfural has a number of industrial uses, including the manufacture of other furans, the manufacture of tetrahydrofuran compounds, and as a solvent for separating saturated from aromatic compounds in petroleum lubricating oil, gas oil, diesel fuel, and vegetable oil, to name but a few of the industrial uses. A problem associated with the use of furfural, however, is its tendency to oxidize in the presence of atmospheric oxygen to form oxidation products such as furoic acid or formyl acrylic acid or formic acid which further, upon heating, forms furfural acidic polymers. The oxidation products and the polymers are undesirable because they lead to a number of problems including corrosion of metal equipment, deposition of corrosion byproducts and acidic polymers on equipment surface. This leads to serious operational problems such as restricting flow of fluids. Because of leakage, storage and dissolved air in the system, it is extremely difficult to prevent air from contacting the furfural in manufacture, storage, transportation and use. All of these factors, alone or in combination, reduce the effectiveness of the end use of the furfural as a solvent in petroleum refining.

Efforts to reduce the undesired oxidation of furfural and its derivatives have involved the use of a variety of compounds as illustrated by the following U.S. Patents:
(a) U.S. Pat. No. 2,382,207 discloses the use of furfuramide,
(b) U.S. Pat. No. 2,384,238 discloses the use of butyramide,
(c) U.S. Pat. No. 2,426,147 discloses the use of hydrosulfite,
(d) U.S. Pat. No. 2,382,207 discloses the use of ammonia,
(e) U.S. Pat. No. 4,045,332 discloses the use of dialkyl anilins for preventing degradation of furfural in solvent extraction,
(f) U.S. Pat. No. 4,433,155 discloses the use of epoxy compounds.

Foreign patents and patent applications also disclose antioxidant compounds for use in furfural:
(a) EP 467,843 A2 and EP 467,844 A2 disclose the use of hindered phenolic compounds and amine compounds, and
(b) Japanese 60090 295A also discloses the use of phenolic compounds as a corrosion inhibitor in furfural/oil mixtures.

As indicated above, the method of the present invention involves the use of phenelenediamines and naphthalenediamines and their derivatives. A number of references disclose a variety of uses of these aromatic diamines:
(a) U.S. Pat. No. 4,466,905 discloses phenylenediamines as a polymerization inhibitor for vinyl aromatic compounds such as styrene, divinylbenzene, vinyltoluene, vinyl naphthalene and polyvinylbensenes;
(b) U.S. Pat. No. 4,664,845 discloses the use of phenelene-diamine as a solvent enhancer for dinitrophenol in an aromatic hydrocarbon; and
(c) JP 49133336 discloses the use of dialkylphenyldiamines as a stabilizer for vinylidine compounds.

SUMMARY OF THE INVENTION

The method of the present invention involves the use of phenylenediamines or naphthalenediamines and their substituted derivatives as antioxidants in furfural or furfural derivatives. The antioxidant is used in sufficient quantities to inhibit the oxidation and/or polymerization of the furfural or its derivatives. The preferred inhibitor is a dialkylphenylenediamine or a dialkylnaphthalenediamene. The most preferred inhibitor is a dialkylphenylenediamine wherein the alkyl groups each contain from 1 to 4 carbon atoms.

DESCRIPTION OF THE DRAWING

The Drawing is a plot of acid formation in furfural vs. time comparing no treatment with treatment by the method of the present invention.

DESCRIPTION OF THE PREFERRED EMBODIMENT

As indicated above, the present invention relates to the treatment of furfural and other furan compounds that are susceptible to oxidation, degradation or polymerization to inhibit such oxidation, degradation and polymerization. The treatment involves the use of phenylenediamines or naphthalenediamines and derivatives thereof. These compounds with aromatic nuclei may be used alone, or in a suitable solvent, or with other inhibitors for furfural such as phenolic antioxidants. The furfural and other furan compounds treated in accordance with the method of the present invention are discussed in detail below.

Furfural and Other Furan Compounds

The method of the present invention is specifically directed to the treatment of furfural and furan compounds that exhibit a tendency to oxidize or polymerize in the presence of oxygen. Furfural is the preferred compound treated, but other derivatives such as furan, furfural alcohol, tetrahydrofurfural, tetrahydrofuran acid, and other compounds characterized by a doubly unsaturated ring of four carbon atoms and one oxygen atom. Although the present invention will be described with specific reference to furfural, it is expressly intended that the invention also have application with the other furan compounds.

The present invention describes the use of phenylenediamine or naphthalenediamine as inhibitor for furfural during the manufacture, storage or use of furfural.

Inhibitors

The inhibitors useful in the method of the present invention fall into two general groups, both of which include aromatic nuclei. The preferred inhibitors are the phenylenediamines. The amino groups on the phenyl ring may be at the ortho, meta or para positions. The general formula of the alkyl and aryl derivatives is as follows:

where:

ARYL is selected from the group consisting of phenyl and naphthyl groups, and $R_1$ and $R_2$ are independently alkyl groups having from 1 to 6 C atoms, preferably 2 to 4 C atoms, or aryl groups having from 1 to 2 phenyl groups.

The locations of the amino groups may be in the ortho (1,2 diamine), meta, (1,3 diamine), or para (1,4 diamine) position, but preferably are in the para position.

Specific phenylenediamines useable in the method of the present invention include the following: N,'N-dimethyl-O-phenylendiamines, N,'N-dimethyl-m-phenylenediamine, N,'N-diphenyl-m-phenylenediamine, N,'N di-2-naphthyl-m-phenylene-diamine, N,'N-dimethyl-p-phenylenediamine, N,'N-diethyl-p-phenylenediamine, N,'N-(sec-butyl) p-phenylenediamine, N,'N-(sec-butyl)-O-phenylenediamine, N-phenyl-p-phenylenediamine, N,'N-diphenyl-p-phenylenediamine, N,'N-di-2-naphthyl-p-phenylenediamine, N-phenyl, 'N-(sec-butyl)-P-phenyldiamine, $N_1N^1$-di-t-butyl-phenylenediamine, N,'N-bis-(1-methyl heptyl)-p-phenylenediamine, deoctyl diphenylamine, and N-isopropyl-'N-diphenyldiamine. The method of preparing these phenyldiamines is well known to those skilled in the art. For example, see KIRK-Othmer Encyclopedia of Chemical Technology, Third Edition, Volume 15, page 216.

Useable phenylenediamines also include the derivatives such as toluenediamines: toluene-2, 4-diamine; toluene-2, 5-diamine; and toluene-3, 4-diamene.

Specific naphthalenediamines include tetramethyl 1,5-naphthalenediamine.

The preferred inhibitors are the dialkylphenylenediamines having the following formula:

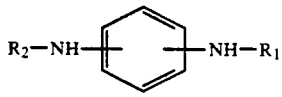

where $R_1$ and $R_2$ are independently alkyl groups (straight or branched) having from 1 to 6 carbon atoms, preferably from 2 to 4 carbon atoms.

The most preferred inhibitor is N, 'N-(sec-butyl) ppheny-lenediamine.

The phenylenediamines and naphthalenediamines described above include substituted compounds where the H atom has been replaced by an alkyl group or other substituent.

Availability

The phenylenediamines and naphthalenediamines and their derivatives are commercially available such as Dupont Antioxidant 22, UOP 5, and UOP 688 (dialkylphenylenediamines). They may be prepared by methods well known in the art.

Method of Use

As indicated above, the inhibitor or inhibitor formulation containing the phenylenediamines or naphthalenediamines or derivatives thereof may be introduced into the furfural or furfural derivative stream in an amount to retard oxidation and/or polymerization of the furfural compounds. With specific reference to the furfural compound, the inhibitor is introduced into the compound at a concentration ranging from 5 to 1000 ppm, preferably 10-500 ppm. The inhibitor may be introduced during the manufacture of the furfural or after manufacture, prior to transportation and/or storage.

The inhibitor also may be introduced into the furfural at the place of use, (e.g. to treat the furfural stream of a system for solvent refining of lubricating oils.

In a particularly preferred embodiment of the method of the present invention, the inhibitor is introduced into a continuously circulating furfural extract stream. In the refining of lubricating oils by solvent extraction, furfural is brought into contact with a lubricating oil in a counter-flow tower. The furfural extracts the low viscosity index constituents and resins and exits the tower bottoms. The furfural stream flows to a furfural recovery unit where the impurities are separated from the furfural, by extraction and stripping, and recycled to the lube oil furfural counter-flow extraction tower. Because of the high temperature extraction and the long life of the furfural in the recirculation stream through the system, it is extremely important that any inhibitor used be effective at the extraction temperatures for long periods of time. In accordance with a preferred embodiment of the present invention, the inhibitor is introduced into the continuous furfural stream downstream of the extraction tower and upstream of the furfural extraction unit. Effective inhibition in solvent lubricating oil extraction is essential because of the presence of air dissolved in the lube oil (generally between 10 to 1,000 ppm) and air leakage into the system.

Although the inhibitor may be used in substantially pure form (i.e. without a solvent), it can also be used in a formulation which includes other compounds such as solvents, dispersants, or other antioxidants. Antioxidants include phenolic antioxidants such as dialkylated phenol. The dispersants include those used for dispersing organic compounds such as lube oil dispersants. A par-ticularly useful dispersant is PIBSA-PAM (polyisobutylene succinic anhydride reacted with (a) a polyamine as described in U.S. Pat. No. 3,804,763 or (b) polyethylene amine).

In the treatment of furfural it is preferred to adjust the pH of the furfural to near neutral (pH of 6.6 to 7.2), because the presence of acids in the stream catalyzes the oxidation of furfural into acid and furfural polymers. The neutralization of the furfural may be achieved by the addition of a solid base such as lime or hydroxides (e.g. KOH) or liquid base such as amines. The preferred bases are KOH and an amine such as diethylenetriamine (DETA), triethanolamine (TEA), ethylenediamine (EDA), morphaline, or combinations of these.

The procedure involves first neutralizing the furfural stream with a suitable base followed by the addition of the inhibitor or inhibitor formulation. The inhibitor dispersant and antioxidant can be introduced into the system as a formulation or can be injected independently.

EXPERIMENTS

Experiment I: This test was carried out to demonstrate the tendency of furfural to oxidize at room temperature (60°-70° F.). A 500 ml sample of furfural was placed in an open flask (exposed to air) and shaken at room temperature for fifty days. The acid number of the furfural sample, at various times, was determined by potentiometric titration and the polymer content was determined by evaporating the unreacted furfural and weighing the residue. The time intervals and data for each measurement are shown in Table I.

TABLE I

| Days | 0 | 1 | 4 | 10 | 15 | 22 | 28 | 36 | 44 | 50 |
|---|---|---|---|---|---|---|---|---|---|---|
| Acid No.* | 0.08 | 0.2 | 1.0 | 2.5 | 4.0 | 6.0 | 9.0 | 16.0 | 22.0 | 30.0 |

*mg KOH/gr.
The increase in the Acid No. is a measure of the acid generation during the air oxidation.

Series II Experiments: Tests were carried out to demonstrate the tendency of furfural to form polymer in the presence of air and at elevated temperatures.

Furfural samples (A, B, C, and D) were placed in separate 100 ml glass containers. Each container was oxidized with air at 25 psig and at a different temperature. The reaction mixture was cooled, filtered and the amount of polymer formed was measured by evaporating the unreacted furfural and measuring the residue. The data are presented in Table II. Similar tests were carried out with furfural samples (E, F, G, and H) at the same temperature in 25 psig of nitrogen atmosphere.

TABLE II

| Furfural Sample | Reaction Time (Hrs.) | Reaction Temp. (°F.) | Polymer Formation (mg/100 ml) |
|---|---|---|---|
| A | 2.0 | 100 | 4.1 |
| B | 2.0 | 200 | 14.6 |
| C | 2.0 | 300 | 110.0 |
| D | 2.0 | 400 | 887.0 |
| E | 2.0 | 100 | 1.5 |
| F | 2.0 | 200 | 3.3 |
| G | 2.0 | 300 | 10.9 |
| H | 2.0 | 400 | 18.8 |

The Table II data demonstrate the significant role of oxygen and high temperatures on polymer formation in furfural. The samples (A, B, C, and D) in the air environment exhibited much more oxidation and polymer formation than the samples (E, F, G, and H) tested in the nitrogen environment at corresponding temperatures.

Series III Experiments: Tests similar to Series II conditions for Sample C were carried out, except the furfural samples contained varying amounts of an inhibitor (di-t-butyl phenylenediamine). The data for the samples containing the inhibitor (I, J, K, and L) are presented in Table III. Prior to commencing the tests, the inhibitor was introduced into each sample and dispersed therein by shaking.

TABLE III

| Sample | Concentration of inhibitor (ppm) | Reaction Time (hrs.) | Reaction Temp. (°F.) | Polymer formed (mg/100 ml) |
|---|---|---|---|---|
| Blank | 0 | 2.0 | 300 | 887 |
| I | 0 | 2.0 | 300 | 408 |
| J | 100 | 2.0 | 300 | 391 |
| K | 250 | 2.0 | 300 | 266 |
| L | 1000 | 2.0 | 300 | 1.3 |

The data in Table III indicates the dramatic effect the dialkylphenylenediamines had on inhibiting the formation of polymer in furfural.

Series IV Experiments

Tests similar to Series III Experiments were carried out, comparing the performance of dialkylphenylenediamine with known furfural antioxidants (Samples N, O, P). These data are presented in Table IV. (All tests were carried out in air (25 psig) at 300° F. and for 4 hours).

TABLE IV

| Sample | Inhibitor | Conc. (ppm) | Acid Gen. (mg.KOH/gr.) | Polymer (mg/100 ml) |
|---|---|---|---|---|
| Blank | None | 0 | 1.6 | 601 |
| M | phenylenediamine[1] | 500 | 1.1 | 169 |
| N | topanol[2] | 500 | 1.3 | 283 |
| O | DNPC[3] | 500 | 1.4 | 331 |
| P | BHT[4] | 500 | 1.8 | 450 |

[1] di-t-butyl phenylenediamine
[2] phenolic antioxidant
[3] di-nitro-p-cresol
[4] di-butyl methyl phenol The Table IV data demonstrates the surprising results obtained with the dialkylphenylenediamines vis-a-vis the commercial antioxidants.

Series V Experiments

These tests compared the generation of acid in oxidized furfural with inhibitor and without inhibitor. Samples of freshly distilled furfural were placed in separate containers—one without any inhibitor and the other with 100 ppm of dialkylphenylenediamine (Sample M). The samples were shaken to permit contact with air for fifty days. The temperature ranged from 60° to 70° F. Acid formation in each sample was determined at various times during the experiment. The data are presented in Table V.

TABLE V

| Days | 0 | 4 | 10 | 15 | 22 | 28 | 36 | 44 | 50 |
|---|---|---|---|---|---|---|---|---|---|
| Furfural | 0.99 | 1.25 | 1.76 | 2.98 | 5.63 | 9.1 | 16.1 | 22.3 | 29.6 |
| Furfural with Inhibitor | 1.00 | 1.25 | 1.76 | 2.49 | 3.23 | 4.2 | 5.7 | 6.9 | 7.9 |

The Table V data, presented graphically in the Drawing, demonstrate the effects of time on acid generation in furfural. In the samples without inhibitor acid generation increased at an accelerated rate as is apparent from the Drawing. However, with the inhibited sample, acid formation increased at a gradual rate throughout the test period. The Drawing shows the acceleration of the furfural oxidation with time when not treated. For the first 17 days, the acid formation in the furfural increases at a steady rate of about 0.15 mg KOH/day. After 17 days, the increase accelerates to almost 1 mg KOH/day. The rate of acid formation in the final 22 days of the test was about 560% higher than that in the first 22 days.

The acid formation in the furfural with the inhibitor remained at the same low rate of 0.15 mg KOH/day throughout the 50 day test period. These tests demonstrate the long term effect of the inhibitor in reducing acid formation used in accordance with the method of the present invention. The long term efficacy of the inhibitor is important because furfural generally has a long use life in many industrial applications (e.g. recycled solvent for refining lube oil).

What is claimed is:

1. A method of inhibiting oxidation of furfural which comprises the steps of (a) adjusting the pH of the furfural to between 6.6 and 7.2, and (b) introducing into the furfural an effective amount of an inhibitor selected from the group consisting of dialkylphenylenediamines, diarylphenylenediamines, dialkylnaphthalenediamines, and diarylnaphthalenediamines.

2. The method of claim 1 wherein the inhibitor is a dialkylphenylenediamine wherein each alkyl group contains from 1 to 6 carbon atoms.

3. The method of claim 1 wherein the inhibitor is di-secbutylphenylenediamine.

4. The method of claim 3 wherein the inhibitor is present in the furfural at a concentration of 5 to 1000 ppm.

5. The method of claim 1 wherein the inhibitor has the following formula:

$$R_2-NH-ARYL-NH-R_1$$

where $R_1$ and $R_2$ are independently alkyl groups containing from 1 to 6 carbon atoms; and ARYL is selected from the group consisting of phenyl and naphthyl groups.

6. The method of claim 1 wherein the inhibitor has the following formula:

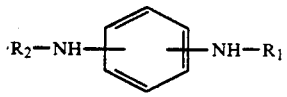

where $R_1$ and $R_2$ are independently alkyl groups containing from 2 to 4 carbon atoms.

7. The method of claim 6 wherein the inhibitor is a dialkylpara-phenylenediamine.

8. The method of claim 7 wherein the inhibitor is di-t-butyl phenylenediamine.

9. In the solvent refining of lubricating oils wherein a continuously circulating furfural stream is brought into contact with lubricating oil to extract constituents therefrom, a process for inhibiting oxidation of the furfural which comprises (a) adjusting the pH of the furfural stream to between 6.6 and 7.2 and (b) injecting into the stream an effective amount of a dialkylphenylenediamine to inhibit the oxidation of the furfural.

10. The method of claim 9 wherein the dialkylphenediamine is dialkyl-para-phenylenediamine.

11. The method of claim 9 wherein the dialkylphenylenediamine is di-t-butyl-para-phenylenediamine.

12. The method of claim 9 wherein the lubricating oil has dissolved therein from 10 to 1000 ppm of air.

13. The method of claim 12 wherein the dialkylphenylenediamine is injected to provide a concentration of 10 to 500 ppm in the furfural.

14. The method of claim 9 wherein the phenylenediamine is N-'N-(sec-butyl) Pphenylenediamine.

* * * * *